(12) United States Patent
Chen et al.

(10) Patent No.: US 12,169,171 B2
(45) Date of Patent: Dec. 17, 2024

(54) METHOD AND DEVICE FOR MEASURING SAND CONTENT IN MISCIBLE PHASE FLUID

(71) Applicant: Chengdu Sea Pioneers Technology Co., Ltd., Chengdu (CN)

(72) Inventors: Jige Chen, Chengdu (CN); Bin Xu, Chengdu (CN); Chao Luo, Chengdu (CN)

(73) Assignee: Chengdu Sea Pioneers Technology Co., Ltd., Chengdu (CN)

( * ) Notice: Subject to any disclaimer, the term of this patent is extended or adjusted under 35 U.S.C. 154(b) by 238 days.

(21) Appl. No.: 18/090,609

(22) Filed: Dec. 29, 2022

(65) Prior Publication Data
US 2023/0204499 A1 Jun. 29, 2023

(30) Foreign Application Priority Data
Dec. 29, 2021 (CN) .......................... 202111643578.5

(51) Int. Cl.
*G01N 21/31* (2006.01)
*G01N 21/85* (2006.01)

(52) U.S. Cl.
CPC ............. *G01N 21/31* (2013.01); *G01N 21/85* (2013.01); *G01N 2201/12746* (2013.01)

(58) Field of Classification Search
CPC ................... G01N 21/31; G01N 21/85; G01N 2201/12746
See application file for complete search history.

(56) References Cited

U.S. PATENT DOCUMENTS

| 4,788,852 A | * | 12/1988 | Martin | G01N 23/12 73/861.04 |
| 2007/0110214 A1 | * | 5/2007 | Bates | G01N 23/2076 378/45 |
| 2010/0238445 A1 | * | 9/2010 | Roux | G16C 20/20 356/436 |

FOREIGN PATENT DOCUMENTS

| CN | 201335814 Y | * | 10/2009 |
| CN | 201347749 Y | * | 11/2009 |
| CN | 103399025 A | * | 11/2013 |

* cited by examiner

*Primary Examiner* — Jonathan M Hansen
*Assistant Examiner* — Jarreas C Underwood
(74) *Attorney, Agent, or Firm* — Cooper Legal Group, LLC

(57) ABSTRACT

Disclosed are a method and a device for measuring a sand content in a miscible phase fluid, the method comprising: flowing of the miscible phase fluid out of an oil and gas well through a pipeline, the miscible phase fluid of the wellhead of the oil and gas well including at least two fluid media; carrying out a measurement with a light quantum of four levels on the miscible phase fluid by a phase separator installed on the pipeline, such that a linear mass of each fluid medium is obtained; calculating a sand content in mass fraction based on the linear mass of all the fluid media, when the fluid media in the miscible phase fluid includes a solid phase sand.

9 Claims, 3 Drawing Sheets ptimethod for measuring sand content in miscible phase

METHOD AND DEVICE FOR MEASURING SAND CONTENT IN MISCIBLE PHASE FLUID

CROSS-REFERENCE TO RELATED APPLICATION

This application claims the priority and benefit of Chinese patent application serial no. 202111643578.5, filed on Dec. 29, 2021. The entirety of Chinese patent application serial no. 202111643578.5 is hereby incorporated by reference herein and made a part of this specification.

TECHNICAL FIELD

The present disclosure relates to the technical field of measurement of industrial miscible phase fluid, in particular to a method and device for measuring sand content in miscible phase fluid.

BACKGROUND

Oil is a fluid mineral buried deep underground. At first, people called the oily liquid mineral produced in nature as petroleum, the combustible gas as natural gas, and the solid combustible oil mineral as asphalt. With further study on these minerals, it is recognized that they are all hydrocarbon compounds in composition and genetically interdependent with each other, so they are collectively called as petroleum.

In the production process of oil, gas and water wells, due to excessive production pressure difference, unconsolidated rock of sandstone reservoir and other reasons, reservoir sand will flows into a wellbore, blocking the oil and gas channels and causing shutdown of oil and gas wells. Since the oilfield development is carried out in deep stratum, sanding in the deep stratum cannot be directly observed, so it can only be prevented by real-time monitoring the sand content in the miscible phase fluid.

However, the traditional method for monitoring sand content cannot be realized by real-time monitoring. Frequent monitoring requires a lot of manpower and time for sampling, separating and testing, leading to relatively high cost.

SUMMARY

A method and device for measuring a sand content in a miscible phase fluid are disclosed, in order to solve the following technical problem, measurement of a sand content in mass fraction in a miscible phase fluid requires a lot of manpower and time, which leads to relative higher cost.

In one aspect of the present disclosure, a method for measuring a sand content in a miscible phase fluid utilizes the flowing technical solutions:

a method for measuring a sand content in a miscible phase fluid, comprising:
flowing of the miscible phase fluid out of an oil and gas well through a pipeline, the miscible phase fluid including at least two fluid media;
carrying out a measurement with a light quantum of four levels on the miscible phase fluid by a phase separator installed on the pipeline, such that a linear mass of each fluid medium is obtained;
calculating a sand content in mass fraction based on the linear mass of all the fluid media, when the fluid media in the miscible phase fluid includes a solid phase sand.

In the above technical solution, in the process of oil exploitation, after completion of the oil and gas well, the miscible phase fluid flows out of the oil and gas well during production. The fluid media in the miscible phase fluid of the oil and gas well may include oil, gas, liquid, etc.; and further may include solid phase sand because formation sands flows into the wellbore due to excessive production pressure difference, unconsolidated rock of sandstone reservoir and other reasons, wherein existence of the solid phase sand may block the oil and gas channels, causing shutdown of oil and gas wells. Therefore, it is necessary to install a phase separator on the pipeline, which can conduct a measurement with a light quantum of four levels on the miscible phase fluid in the pipeline by emitting four groups of light quanta of different levels, calculating the linear quality of each fluid medium. Since solid phase sand does not exist all the time, but is discontinuous and discrete, only when the fluid media in the miscible phase fluid includes solid phase sand, the sand content in mass fraction is calculated according to the linear mass of all the fluid media. The phase separator is arranged on the pipeline and carries out measurement by four groups of light quanta with different levels. It is not necessary to sample and separate the solid phase sand in the miscible phase fluid, to obtain the sand content in mass fraction, reducing labor and time consumption and reducing costs.

Optionally, the light quantum of four levels includes a light quantum of first level, a light quantum of second level, a light quantum of third level and a light quantum of fourth level,
wherein energy of the light quantum of first level is 31 keV, energy of the light quantum of second level is 81 keV, energy of the light quantum of third level is 160 keV, and energy of the light quantum of fourth level is 356 keV.

In the above technical solution, there are four levels of light quantum in the phase separator, wherein energy of the first level of light quantum is 31 keV, the energy of the second level of light quantum is 81 keV, the energy of the third level of light quantum is 160 keV, the energy of the fourth level of light quantum is 356 keV. A known Ba-133 light quantum source has a radioactivity of 25 microcurie, can emit nearly one million single light quanta of the energy groups 31 keV, 81 keV, 160 keV and 356 keV. Through the measurement of energy of each light quantum, the measurement of phase fraction of the miscible phase fluid is completed according to the photoelectric cross section of the light quantum group of material and the energy of 31 keV, 81 keV and 160 keV, and Compton cross section of the light quantum group of material and energy of 356 keV.

Optionally, a step of carrying out a measurement with a light quantum of four levels on the miscible phase fluid by a phase separator installed on the pipeline, such that a linear mass of each fluid medium is obtained comprises:
emitting the light quantum of first level, the light quantum of second level, the light quantum of third level and the light quantum of fourth level by the phase separator installed on the pipeline;
detecting a measured transmission quantity of the light quantum of four levels corresponding to each fluid medium;
obtaining a ratio between medium-free transmission quantities of the light quantum of four levels according to a characteristic of a light quantum source, wherein the medium-free transmission quantity is a transmission quantity of corresponding light quantum of level group when the pipeline is empty and there is no medium in the pipeline;

obtaining a linear mass absorption coefficient of the light quantum of first level, of the light quantum of second level and of the light quantum of third level corresponding to each fluid medium, as well as the Compton scattering constant of the light quantum of fourth level;

calculating the linear mass of each fluid medium according to the measured transmission quantity, ratio between medium-free transmission quantities, the linear mass absorption coefficient and the Compton scattering constant.

In the above technical solution, the phase separator can emit the light quantum of first level, the light quantum of second level, the light quantum of third level and the light quantum of fourth level through the Ba-133 light quantum source; the measured transmission quantity of light quantum of each level group passing through the miscible phase fluid is detected and received by the light quantum probe; and the ratio between medium-free transmission quantities of the light quantum of four levels is obtained according to a characteristic of a light quantum source, wherein the medium-free transmission quantity is a transmission quantity of the light quantum of corresponding level group when the pipeline is empty and there is no medium in the pipeline; a linear mass absorption coefficient of the light quantum of first level, the light quantum of second level and the light quantum of third level corresponding to each fluid medium is obtained, as well as the Compton scattering constant of the light quantum of four levels; the linear mass of each fluid medium is calculated according to the measured transmission quantity, ratio between medium-free transmission quantities, the linear mass absorption coefficient and the Compton scattering constant. It should be noted that the ratio between medium-free transmission quantities is set by the inherent characteristic of the light quantum source. The linear mass absorption coefficient and Compton scattering constant are both calibration values, that is, they can be calculated through pre-calibration calculation.

Optionally, a step of obtaining a ratio between medium-free transmission quantities of the light quantum of four levels according to a characteristic of a light quantum source comprises:

determining the medium-free transmission quantity of the light quantum of first level as $N_{0,1}$, the ratio between the medium-free transmission quantity of the light quantum of second level $N_{0,2}$ and the $N_{0,1}$ as $f_2$, the ratio between the medium-free transmission quantity of the light quantum of third level $N_{0,3}$ and the $N_{0,1}$ as $f_3$, and the ratio between the medium-free transmission quantity of the light quantum of fourth level $N_{0,4}$ and the $N_{0,1}$ as $f_4$ according to the characteristic of the light quantum source.

In the above technical solution, there is ratio between the inherent characteristics of Ba-133 light quantum source and the medium-free transmission quantities of the light quantum of different level groups $N_{0,2}=f_2N_{0,1}$, $N_{0,3}=f_3N_{0,1}$, $N_{0,4}=f_4N_{0,1}$, wherein $f_2$, $f_3$ and $f_4$ are known proportional coefficient, which are a natural constant coefficient and does not change with any measurement conditions. Because of existence of the proportional coefficients, three unknown quantities $N_{0,1}$, $N_{0,2}$, $N_{0,3}$ and $N_{0,4}$ can actually be regarded as one unknown quantity $N_{0,1}$, thus eliminating the need for measurement or calibration of $N_{0,1}$. Since $N_{0,1}$ is not required to be calibrated, influence of temperature drift in the light quantum probe on the measurement is fundamentally avoided, thereby it isn't necessary to arrange a thermostat in the light quantum probe, which saves equipment costs while eliminating calibration of the medium-free transmission quantity.

Optionally, a step of obtaining linear mass absorption coefficients of the light quantum of first level, the light quantum of second level and the light quantum of third level corresponding to each fluid medium, as well as the Compton scattering constant of the light quantum of fourth level comprises:

controlling the phase separator to emit the light quantum of first level, the light quantum of second level, the light quantum of third level and the light quantum of four levels when the pipeline is filled with a single fluid medium.

detecting a single-fluid-medium transmission quantity $N_{x,1}$ of the light quantum of first level, a single-fluid-medium transmission quantity $N_{x,2}$ of the light quantum of second level, a single-fluid-medium transmission quantity $N_{x,3}$ of the light quantum of third level, and a single-fluid-medium transmission quantity $N_{x,4}$ of the light quantum of fourth level;

calculating a linear mass absorption coefficient of a single fluid medium of the light quantum of first level $\alpha_{x,1}$ according to a photoelectric absorption equation of a single fluid medium and the medium-free transmission quantity of the light quantum of first level $N_{0,1}$;

calculating a linear mass absorption coefficient of a single fluid medium of the light quantum of second level $\alpha_{x,2}$ according to a photoelectric absorption equation and the medium-free transmission quantity of a single fluid medium of the light quantum of second level $N_{0,2}$;

calculating a linear mass absorption coefficient of a single fluid medium of the light quantum of third level $\alpha_{x,3}$ according to a photoelectric absorption equation and the medium-free transmission quantity of a single fluid medium of the light quantum of third level $N_{0,3}$;

obtaining a Compton scattering constant K according to a Compton scattering characteristic of the light quantum of fourth level.

In the above technical solution, the calculation principle of the calibration value of the linear mass absorption coefficient of each fluid medium is: filling the pipeline with a single fluid medium, controlling the phase separator to emit the light quantum of first level, the light quantum of second level, the light quantum of third level and the light quantum of fourth level; detecting the single-fluid-medium transmission quantity $N_{x,1}$ of the light quantum of first level, the single-fluid-medium transmission quantity $N_{x,2}$ of the light quantum of second level, the single-fluid-medium transmission quantity No of the light quantum of third level, and the single-fluid-medium transmission quantity $N_{x,4}$ of the light quantum of fourth level by the light quantum probe; calculating the linear mass absorption coefficient of a single fluid medium of the light quantum of each level group $\alpha_{x,1}$, $\alpha_{x,2}$, $\alpha_{x,3}$ according to the photoelectric absorption equation of a single fluid medium of the light quantum of different level group and the corresponding medium-free transmission quantity; since the secondary radiation ray after Compton scattering is dependent on the scattering angle but independent on scattering material, the Compton scattering constant K is obtained for the Compton scattering characteristic of the light quantum of fourth level.

Optionally, a step of calculating a linear mass absorption coefficient of a single fluid medium of the light quantum of first level $\alpha_{x,1}$ according to a photoelectric absorption equation and the medium-free transmission quantity of a single fluid medium of the light quantum of first level $N_{0,1}$ comprises:

transforming the total equation of photoelectric absorption of each fluid medium of the light quantum of first level into the photoelectric absorption equation of a single fluid medium $$\ln\left(\frac{N_{0,1}}{N_{x,1}}\right) = \alpha_{x,1} Q_x;$$

introducing the medium-free transmission quantity $N_{0,1}$ and the single-fluid-medium transmission quantity $N_{x,1}$ into the photoelectric absorption equation of full oil, to obtain the linear mass absorption coefficient of a single fluid medium of the light quantum of first level $$\alpha_{x,1} = \ln\left(\frac{N_{0,1}}{N_{x,1}}\right) / Q_x.$$

In the above technical solution, assuming that the fluid media in the miscible phase fluid include gas, liquid and sand, the photoelectric absorption equation of the light quantum of first level is $$\ln\left(\frac{N_{0,1}}{N_{x,1}}\right) = \alpha_{g,1} Q_g + \alpha_{l,1} Q_l + \alpha_{s,1} Q_s,$$

where subscript g represents gas phase, subscript 1 represents liquid phase, subscript s represents sand phase, $\alpha_{g,1}$ is the linear mass absorption coefficient of gas, $\alpha_{l,1}$ is the linear mass absorption coefficient of liquid, $\alpha_{s,1}$ is the linear mass absorption coefficient of sand, $Q_g$ is linear mass gas, $Q_l$ is linear mass of liquid, Qs is linear mass of sand. When the pipeline is filled with a single fluid medium, for example, the single fluid medium is a gas phase, the photoelectric absorption equation of a single fluid medium becomes $$\ln\left(\frac{N_{0,1}}{N_{g,1}}\right) = \alpha_{g,1} Q_g, \text{ and } \alpha_{g,1} = \ln\left(\frac{N_{0,1}}{N_{g,1}}\right) / Q_g$$

is obtained after transformation.

Optionally, a step of calculating the linear mass of each fluid medium according to the measured transmission quantity, ratio between medium-free transmission quantities, the linear mass absorption coefficient and the Compton scattering constant comprises:

according to the total equation of photoelectric absorption of each fluid medium of the light quantum of first level, the total equation of photoelectric absorption of each fluid medium of the light quantum of second level, the total equation of photoelectric absorption of each fluid medium of the light quantum of third level and a Compton absorption equation of the light quantum of fourth level;

introducing the measured transmission quantity, the ratio between medium-free transmission quantities, the linear mass absorption coefficient and the Compton scattering constant into the above equation, respectively, to calculate the linear mass of each fluid medium $Q_x$.

In the above technical scheme, according to the total equation of photoelectric absorption of each fluid medium of the light quantum of first level, the total equation of photoelectric absorption of each fluid medium of the light quantum of second level, the total equation of photoelectric absorption of each fluid medium of the light quantum of third level and the Compton absorption equation of the light quantum of fourth level, $N_{0,1}$ and the linear mass of each fluid medium $Q_x$ can be calculated by introducing the measured transmission quantity, the ratio between medium-free transmission quantities, the linear mass absorption coefficient and the Compton scattering constant into the above equation, respectively.

Optionally, before a step of calculating a sand content in mass fraction based on the linear mass of all the fluid media, the method further includes:

judging, if the linear mass of each fluid medium $Q_x$ includes a linear mass of sand of the solid phase sand $Q_s$;

determining, that a fluid medium in the miscible phase fluid includes the solid phase sand, if the linear mass of sand is included;

determining, that the fluid medium in the miscible phase fluid doesn't include the solid phase sand, if the linear mass of mass isn't included.

In the above technical solution, after the linear mass of each fluid medium $Q_x$ has been calculated, the solid phase sand is dispersed in the miscible phase fluid, so it is necessary to judge if the linear mass of each fluid medium $Q_x$ includes a linear mass of and of the solid phase sand $Q_s$. only when the linear mass of sand $Q_s$ exists, the solid phase sand exist, and then, the sand content in mass fraction can be calculated.

Optionally, a step of calculating a sand content in mass fraction based on the linear mass of all the fluid media further includes:

calculating the sand content in mass fraction according to the linear mass of and of the solid phase sand $Q_s$ and the linear mass of all the fluid media $Q_x$;

wherein the sand content in mass fraction is $$SMF = \frac{Q_s}{Q_x}.$$

In the above technical solution, assuming that the linear mass of all the fluid media includes $Q_g$, $Q_l$ and $Q_s$ the sand content in mass fraction will be $$SMF = \frac{Q_s}{Q_g + Q_l + Q_s}.$$

In the second aspect, a device for measuring a sand content in a miscible phase fluid is disclosed, including:
a phase separator, which is installed on a pipeline, wherein a miscible phase fluid flows out of an oil and gas well through the pipeline;
wherein the phase separator is configured to carry out the method for measuring a sand content in a miscible phase fluid according to the first aspect, to obtain a sand content in mass fraction in the miscible phase fluid.

To sum up, the present disclosure includes at least one of the following beneficial technical effects:

1. Because the phase separator is arranged on the pipeline, the miscible phase fluid flows out of the oil and gas well, a measurement with a light quantum of four levels is carried out on the miscible phase fluid in the pipeline, calculating the linear quality of each fluid medium. Since solid phase sand does not exist all the time, but is discontinuous and discrete, only when the fluid media in the miscible phase fluid includes solid phase sand, the sand content in mass fraction can be calculated according to the linear mass of all the fluid media. The phase separator is arranged on the pipeline and carries out a measurement by four groups of light quanta with different levels. It is not necessary to sample and separate the solid phase sand in the miscible phase fluid, to obtain the sand content in mass fraction, reducing labor and time consumption and reducing costs.

2. Through the inherent characteristic of the Ba-133 light quantum source, there is ratio between the medium-free transmission quantities of the light quantum of different level groups, wherein the proportional coefficient is natural constant coefficient and wouldn't change with any measurement conditions. Because of existence of the proportional coefficient, thereby eliminating the need for measurement or calibration of the medium-free transmission quantity corresponding to the light quantum of first level, influence of temperature drift in the light quantum probe on the measurement is fundamentally avoided, thereby it isn't necessary to arrange a thermostat in the light quantum probe, which saves equipment costs while eliminating calibration of the medium-free transmission quantity.

DESCRIPTION OF THE EMBODIMENTS

In order to make the purpose, technical solution and advantages of the present disclosure more clear, it would be further described in detail below through the drawings and embodiments. It should be understood that the embodiments described here are only used to explain, not to limit the present disclosure.

A method for measuring a sand content in a miscible phase fluid is disclosed.

Figure 1:
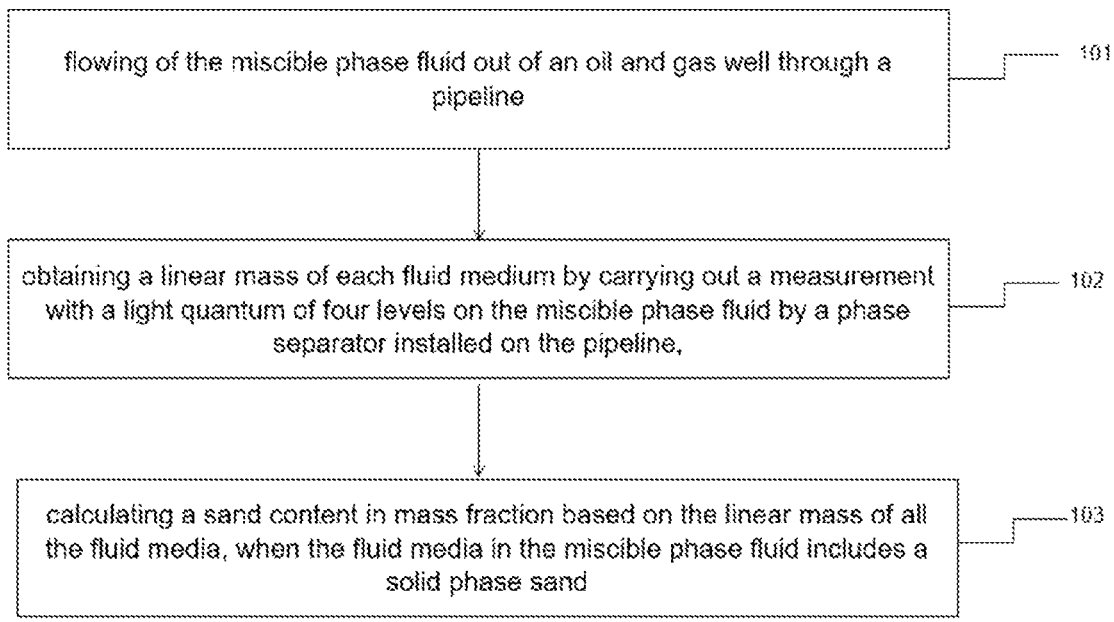
FIG. 1 is a flow diagram of the method for measuring a sand content in a miscible phase fluid of the present disclosure.
Figure 2:
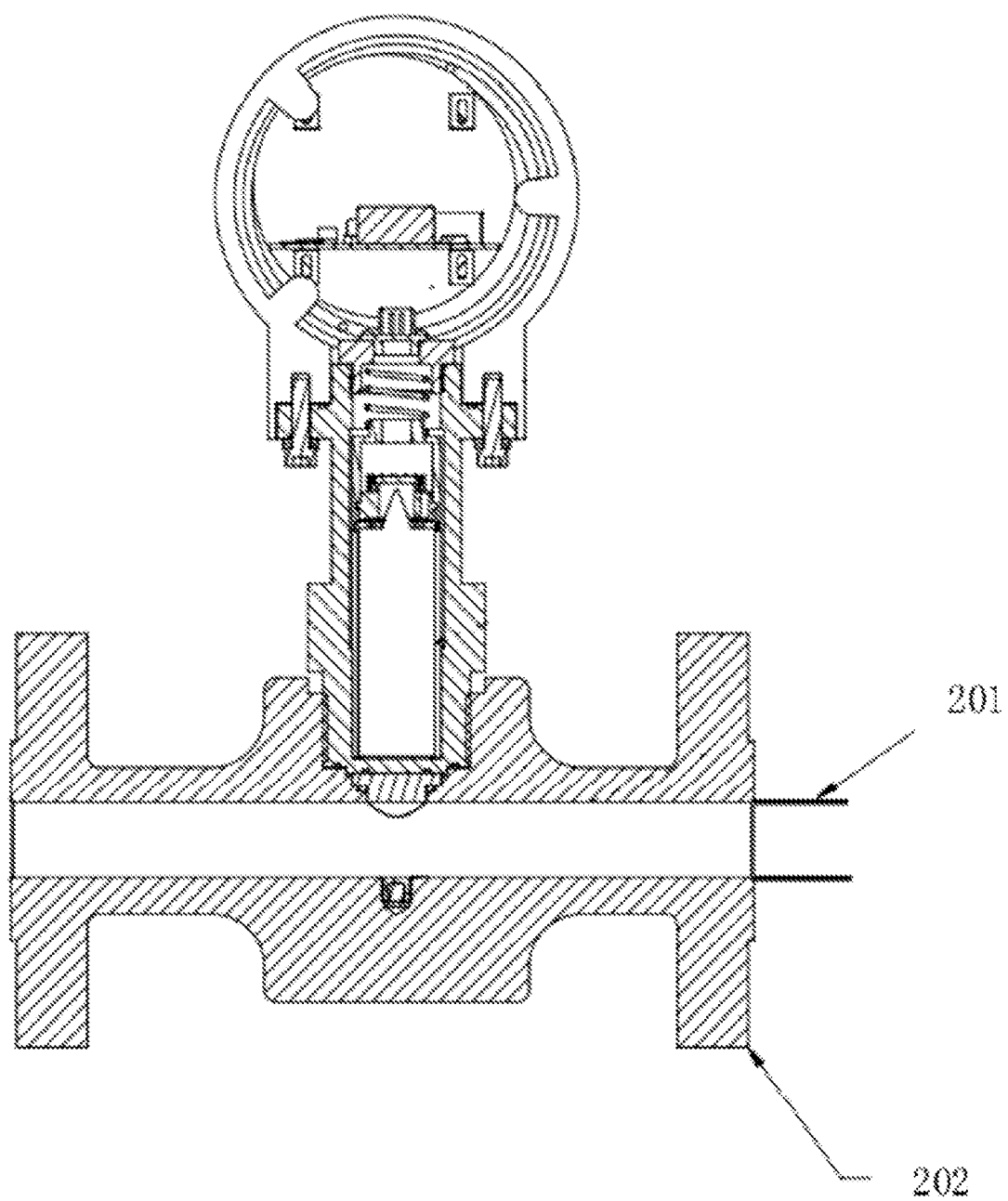
FIG. 2 is a structure diagram of the device for measuring a sand content in a miscible phase fluid of the present disclosure.

Referring to FIG. 1, the method includes:

101, flowing of the miscible phase fluid out of an oil and gas well through a pipeline.

Wherein the device for measuring a sand content in a miscible phase fluid is shown in FIG. 2, wherein the phase separator 202 is installed on the pipeline 201. In the process of oil exploitation, after completion of the oil and gas well, the miscible phase fluid is controlled to flow out of the oil and gas well through arrangement of the pipeline 201. The miscible phase fluid includes at least two fluid media, which can be oil, gas and water, and further includes solid phase sand because formation sands flows into the wellbore due to excessive production pressure difference, unconsolidated rock of sandstone reservoir and other reasons, wherein existence of the solid phase sand may block the oil and gas channels, causing shutdown of oil and gas wells.

102, carrying out a measurement with a light quantum of four levels on the miscible phase fluid by a phase separator installed on the pipeline, such that a linear mass of each fluid medium is obtained.

Wherein the phase separator installed on the pipeline can conduct a measurement with a light quantum of four levels on the miscible phase fluid in the pipeline by emitting four groups of light quanta of different energy levels, so as to obtain the linear quality of each fluid medium.

Specifically, the light quantum is abbreviated as photon, which is elementary particle for transmitting electromagnetic interaction and is a kind of gauge boson. Photon is a carrier of electromagnetic radiation, and in quantum field theory, photon is considered as the medium of electromagnetic interaction. Compared with most elementary particles, the static mass of photon is zero, which means that their propagation velocity in vacuum is the speed of light. Like other quantum, photon has wave-particle duality: photon can show the properties of refraction, interference and diffraction of classical waves; the particle nature of photon can be proved by photoelectric effect. Photon can only transfer quantized energy, which is a lattice particle and a mass energy phase of a loop quantum particle. The energy of a photon is proportional to the frequency of the light wave. The higher the frequency is, the higher the energy is. When a photon is absorbed by an atom, an electron gains enough energy to transition from the inner orbit to the outer orbit, and the atom with electronic transition changes from the ground state to the excited state.

A Ba-133 light quantum source is used in the phase separator, which emits the light quantum of multi-level groups taking four groups as an example, wherein energy of the light quantum of first level is 31 keV, the energy of the light quantum of second level is 81 keV, the energy of the light quantum of third level is 160 keV, the energy of the light quantum of fourth level is 356 keV. A known Ba-133 light quantum source has a radioactivity of 25 microcurie, can emit nearly one million single light quanta of the energy groups 31 keV, 81 keV, 160 keV and 356 keV. Through the measurement of energy of each light quantum, the measurement of phase fraction of the miscible phase fluid is completed according to the photoelectric cross section of the light quantum group of material and the energy of 31 keV, 81 keV and 160 keV, and Compton cross section of the light quantum group of material and energy of 356 keV.

103, calculating a sand content in mass fraction based on the linear mass of all the fluid media, when the fluid media in the miscible phase fluid includes a solid phase sand.

Since solid phase sand does not exist all the time, but is discontinuous and discrete, only when the fluid media in the miscible phase fluid includes solid phase sand, the sand content in mass fraction can be calculated according to the linear mass of all the fluid media.

The implementation principle of the present embodiment is: the phase separator is arranged on the pipeline and carries out measurement by four groups of light quanta with different energy levels. It is not necessary to sample and separate the solid phase sand in the miscible phase fluid, to obtain the sand content in mass fraction, reducing labor and time consumption and reducing costs.

Figure 3:
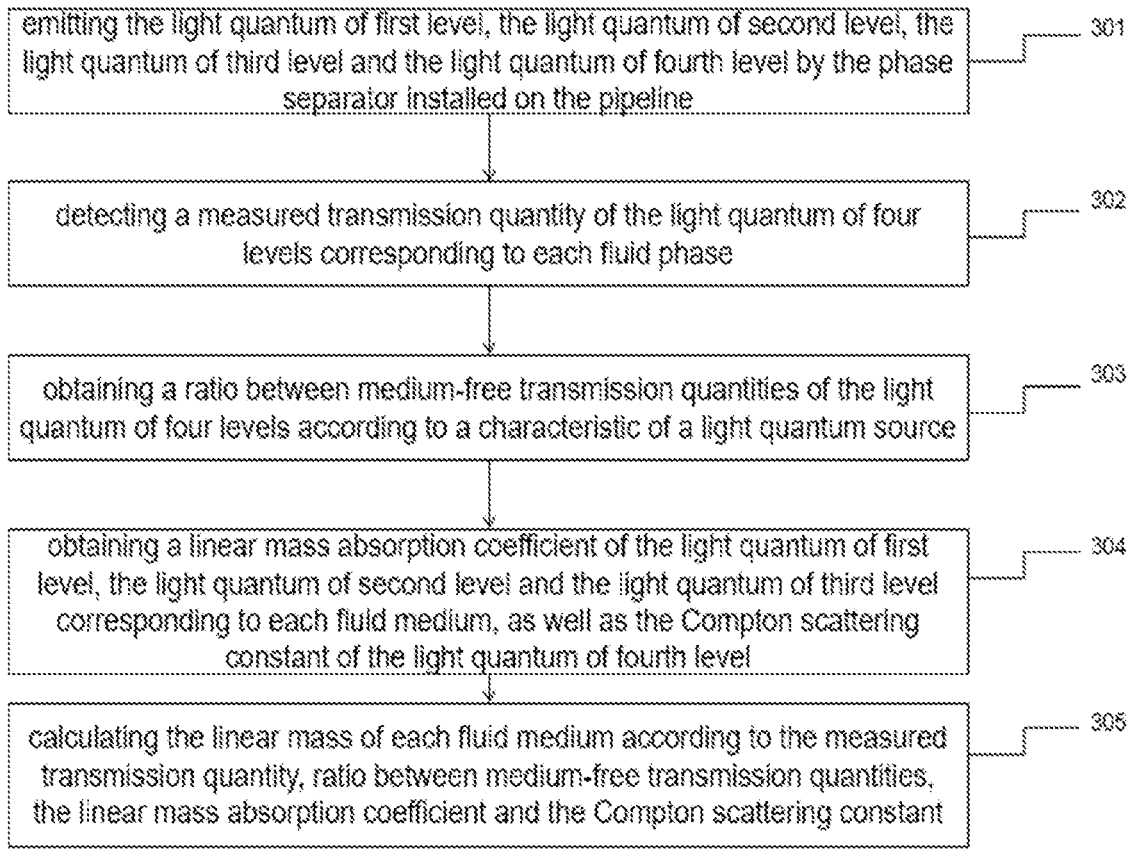
FIG. 3 is a flow diagram of the step of calculating the linear mass of each fluid medium of the present disclosure.

In step 102 of the embodiment in FIG. 1 above, it is Ba-133 light quantum source as the phase separator emits light quantum, wherein energy of the light quantum of first level is 31 keV, the energy of the light quantum of second level is 81 keV, the energy of the light quantum of third level is 160 keV, the energy of the light quantum of fourth level is 356 keV. The linear mass of each fluid medium is concretely calculated as follows:

Referring to FIG. 3, calculating the linear mass of each fluid medium includes: 301, emitting the light quantum of first level, the light quantum of second level, the light quantum of third level and the light quantum of fourth level by the phase separator installed on the pipeline.

According to description of the phase separator in the embodiment shown in FIG. 1, the Ba-133 light quantum source emits energy of the light quantum of first level with 31 keV, the energy of the light quantum of second level with 81 keV, the energy of the light quantum of third level with 160 keV, the energy of the light quantum of fourth level with 356 keV.

302, detecting a measured transmission quantity of the light quantum of four levels corresponding to each fluid phase.

Wherein the measured transmission quantity of light quantum of four levels passing through the miscible phase fluid is received by the light quantum probe

303, obtaining a ratio between medium-free transmission quantities of the light quantum of four levels according to a characteristic of a light quantum source.

Wherein there is ratio between the inherent characteristic of Ba-133 light quantum source and the medium-free transmission quantities of the light quantum of different level groups $N_{0,2}=f_2 N_{0,1}$, $N_{0,3}=f_3 N_{0,1}$, $N_{0,4}=f_4 N_{0,1}$, wherein $f_2$, $f_3$ and $f_4$ are known proportional coefficient, which are natural constant coefficients and do not change with any measurement conditions. Because of existence of the proportional coefficients, three unknown quantities $N_{0,1}$, $N_{0,2}$, $N_{0,3}$ and $N_{0,4}$ can actually be regarded as one unknown quantity $N_{0,1}$, thus eliminating the need for measurement or calibration of $N_{0,1}$. Since $N_{0,1}$ is not required to be calibrated, influence of temperature drift in the light quantum probe on the measurement is fundamentally avoided, thereby it isn't necessary to arrange a thermostat in the light quantum probe, which saves equipment costs while eliminating calibration of the medium-free transmission quantity.

304, obtaining a linear mass absorption coefficient of the light quantum of first level, the light quantum of second level and the light quantum of third level corresponding to each fluid medium, as well as the Compton scattering constant of the light quantum of fourth level.

Wherein the calculation principle of the calibration value of the linear mass absorption coefficient of each fluid medium is:

(1) controlling the phase separator to emit the light quantum of first level, the light quantum of second level, the light quantum of third level and the light quantum of fourth level, when the pipeline is filled with a single fluid medium;

(2) detecting the single-fluid-medium transmission quantity $N_{x,1}$ of the light quantum of first level, the single-fluid-medium transmission quantity $N_{x,2}$ of the light quantum of second level, the single-fluid-medium transmission quantity $N_{x,3}$ of the light quantum of third level, and the single-fluid-medium transmission quantity $N_{x,4}$ of the light quantum of fourth level;

(3) calculating the linear mass absorption coefficient of single fluid medium of the light quantum of first level $\alpha_{x,1}$ according to the photoelectric absorption equation and the medium-free transmission quantity $N_{x,1}$ of single fluid medium of the light quantum of first level group;

assuming that the fluid media in the miscible phase fluid include gas, liquid and sand, the photoelectric absorption equation of the light quantum of first level is $$\ln\left(\frac{N_{0,1}}{N_{x,1}}\right) = \alpha_{g,1} Q_g + \alpha_{l,1} Q_l + \alpha_{s,1} Q_s,$$

where subscript g represents gas phase, subscript l represents liquid phase, subscript s represents sand phase, $\alpha_{g,1}$ is the linear mass absorption coefficient of gas, $a_{l,1}$ is the linear mass absorption coefficient of liquid, $\alpha_{s,1}$ is the linear mass absorption coefficient of sand, $Q_g$ is linear mass of gas, $Q_l$ is linear mass of liquid, $Q_s$ is linear mass of sand. When the single fluid medium is a gas phase, the photoelectric absorption equation of single fluid medium becomes $$\ln\left(\frac{N_{0,1}}{N_{g,1}}\right) = \alpha_{g,1} Q_g, \text{ and } \alpha_{g,1} = \ln\left(\frac{N_{0,1}}{N_{g,1}}\right)/Q_g$$

is obtained after transformation.
Similarly, $$\alpha_{l,1} = \ln\left(\frac{N_{0,1}}{N_{l,1}}\right)/Q_l \text{ and } \alpha_{s,1} = \ln\left(\frac{N_{0,1}}{N_{s,1}}\right)/Q_s$$

are obtained.

(4) calculating the linear mass absorption coefficient of single fluid medium of the light quantum of second level $\alpha_{x,2}$ according to the photoelectric absorption equation and the medium-free transmission quantity of a single fluid medium of the light quantum of second level $N_{0,2}$; similarly as (3).

(5) calculating the linear mass absorption coefficient of single fluid medium of the light quantum of third level $\alpha_{x,3}$ according to the photoelectric absorption equation and the medium-free single-fluid-medium transmission quantity of the light quantum of third level $N_{0,3}$; similarly as (3).

(6) Obtaining a Compton scattering constant K according to a Compton scattering characteristic of the light quantum of fourth level.

Since the secondary radiation ray after Compton scattering is dependent on the scattering angle but independent on scattering material, so for the light quantum of third level with energy of 356 keV, the energy has reached the energy of the Compton effect, and then the Compton scattering property of the light quantum of third level is the Compton scattering constant K, and the Compton absorption equation of each fluid medium of the miscible phase fluid of the light quantum of the third level (with energy of 356 keV) is:

$$\ln\left(\frac{N_{0,4}}{N_{x,4}}\right) = K * (Q_g + Q_l + Q_s)$$

305, calculating the linear mass of each fluid medium according to the measured transmission quantity, ratio between medium-free transmission quantities, the linear mass absorption coefficient and the Compton scattering constant.

Wherein the total equation of photoelectric absorption of each fluid medium of the light quantum of first level is $$\ln\left(\frac{N_{0,1}}{N_{x,1}}\right) = \alpha_{g,1}Q_g + \alpha_{l,1}Q_l + \alpha_{s,1}Q_s,$$

the total equation of photoelectric absorption of each fluid medium of the light quantum of second level is $$\ln\left(\frac{N_{0,2}}{N_{x,2}}\right) = \alpha_{g,2}Q_g + \alpha_{l,2}Q_l + \alpha_{s,2}Q_s,$$

the total equation of photoelectric absorption of each fluid medium of the light quantum of third level is $$\ln\left(\frac{N_{0,3}}{N_{x,3}}\right) = \alpha_{g,3}Q_g + \alpha_{l,3}Q_l + \alpha_{s,3}Q_s,$$

the total equation of photoelectric absorption of each fluid medium of the light quantum of fourth level is $$\ln\left(\frac{N_{0,4}}{N_{x,4}}\right) = K*(Q_g + Q_l + Q_s).$$

because $N_{0,2} = f_2 N_{0,1}$, $N_{0,3} = f_3 N_{0,1}$, $N_{0,4} = f_4 N_{0,1}$, then $\ln\left(\frac{N_{0,2}}{N_{x,2}}\right) = \alpha_{g,2}Q_g + \alpha_{l,2}Q_l + \alpha_{s,2}Q_s = \ln\left(\frac{f_2 N_{0,1}}{N_{x,2}}\right)$ $\ln\left(\frac{N_{0,3}}{N_{x,3}}\right) = \alpha_{g,3}Q_g + \alpha_{l,3}Q_l + \alpha_{s,3}Q_s = \ln\left(\frac{f_3 N_{0,1}}{N_{x,3}}\right)$ $\ln\left(\frac{N_{0,4}}{N_{x,4}}\right) = K*(Q_g + Q_l + Q_s) = \ln\left(\frac{f_4 N_{0,1}}{N_{x,4}}\right)$ $N_{0,1}$, $Q_g$, $Q_l$, $Q_s$ are calculated.

The implementation principle of the present embodiment is: measuring the linear mass of the fluid media in the miscible phase fluid by taking the miscible phase fluid including gas, liquid and sand as an example. In the calculation process, the required linear mass absorption coefficient and Compton scattering constant are calibration values, which can be calibrated and calculated respectively through the pipeline state of full liquid, full gas and full sand. The ratio between the measured transmission quantity and the medium-free transmission quantity can be introduced in the photoelectric absorption equation and Compton absorption equation of the light quantum of four different levels, which can realize linear mass of gas, linear mass of liquid and linear mass of sand.

Optionally, in the embodiment shown in FIG. 1 above, the method further includes before a step of calculating the sand content in mass fraction according to the linear mass of all the fluid media:

judging, if the linear mass of each fluid medium $Q_x$ includes a linear mass of sand of the solid phase sand $Q_s$;

determining, that a fluid media of the miscible phase fluid includes the solid phase sand, if the linear mass of sand is included;

determining, that the fluid media of the miscible phase fluid doesn't include the solid phase sand, if the linear mass of sand isn't included.

The implementation principle of the present embodiment is: after the linear mass of each fluid medium $Q_x$ has been calculated, the solid phase sand may appear indirectly in the miscible phase fluid, so it is necessary to judge if the linear mass $Q_x$ includes a linear mass of sand of the solid phase sand $Q_s$. only when the linear mass of sand $Q_s$ exists, the solid phase sand exists, and then, the sand content in mass fraction can be calculated.

In the embodiment of FIG. 3, a step of calculating a sand content in mass fraction based on the linear mass of all the fluid media after obtaining $Q_g$, $Q_l$ and $Q_s$ further includes:

calculating the sand content in mass fraction according to the linear mass of sand of the solid phase sand $Q_s$ and the linear mass of all the fluid media $Q_x$;

wherein the sand content in mass fraction is $$SMF = \frac{Q_s}{Q_x}.$$

The implementation principle of the present embodiment is: the calculation equation of the content of each fluid medium is:

Gas content in mass fraction $$GMF = \frac{Q_g}{Q_g + Q_l + Q_s}$$

Liquid content in mass fraction, $$LMF = \frac{Q_l}{Q_g + Q_l + Q_s}$$

Sand content in mass fraction, $$SMF = \frac{Q_s}{Q_g + Q_l + Q_s}.$$

Referring to FIG. 2, a device for measuring a sand content in a miscible phase fluid is disclosed, including:

a phase separator 202, which is installed on a pipeline 201, wherein a miscible phase fluid flows out of an oil and gas well through the pipeline 201;

wherein the phase separator 202 is configured to carry out the method for measuring a sand content in a miscible phase fluid according to the above embodiments, to obtain a sand content in mass fraction in the miscible phase fluid.

The above are preferred embodiments of the present disclosure, and the protection scope of the present disclosure is not limited accordingly. Unless otherwise specified, any features disclosed in the present specification (including the abstract and drawings) can be replaced by other equivalent or similar alternative features. That is, unless otherwise stated, each feature is only one example of a series of equivalent or similar features.

What is claimed is:

1. A method for measuring a sand content in a miscible phase fluid, comprising:

passing a miscible phase fluid containing at least two fluid media from an oil and gas well through a pipeline;

carrying out a measurement with a light quantum of four levels on the miscible phase fluid by a phase separator installed on the pipeline to obtain linear masses of the at least two fluid media, wherein:
the light quantum of four levels comprises a light quantum of first level, a light quantum of second level, a light quantum of third level and a light quantum of fourth level, and
the step of carrying out a measurement with a light quantum of four levels on the miscible phase fluid by a phase separator installed on the pipeline to obtain linear masses of the at least two fluid media comprises:
emitting the light quantum of first level, the light quantum of second level, the light quantum of third level and the light quantum of fourth level by the phase separator installed on the pipeline;
detecting a measured transmission quantity of the light quantum of four levels for the at least two fluid media;
obtaining a ratio between medium-free transmission quantities of the light quantum of four levels, wherein the medium-free transmission quantity is a transmission quantity in an empty and medium-free pipeline;
obtaining a linear mass absorption coefficient of the light quantum of first level, the light quantum of second level and the light quantum of third level for the at least two fluid media, and Compton scattering constant of the light quantum of fourth level; and
calculating a sand content in mass fraction in the miscible phase fluid based on the linear masses of the at least two fluid media.

2. The method for measuring a sand content in a miscible phase fluid according to claim 1, wherein energy of the light quantum of first level is 31 keV, energy of the light quantum of second level is 81 keV, energy of the light quantum of third level is 160 keV, and energy of the light quantum of fourth level is 356 keV.

3. The method for measuring a sand content in a miscible phase fluid according to claim 2, wherein the step of obtaining a ratio between medium-free transmission quantities of the light quantum of four levels comprises:
defining the medium-free transmission quantity of the light quantum of first level as $N_{0,1}$, a ratio of the medium-free transmission quantity of the light quantum of second level $N_{0,2}$ to $N_{0,1}$ as $f_2$, a ratio of the medium-free transmission quantity of the light quantum of third level $N_{0,3}$ to $N_{0,1}$ as $f_3$, and a ratio of the medium-free transmission quantity of the light quantum of fourth level $N_{0,4}$ to $N_{0,1}$ as $f_4$.

4. The method for measuring a sand content in a miscible phase fluid according to claim 3, wherein the step of obtaining a linear mass absorption coefficient of the light quantum of first level, the light quantum of second level and the light quantum of third level for the at least two fluid media and Compton scattering constant of the light quantum of fourth level comprises:
controlling the phase separator to emit the light quantum of first level, the light quantum of second level, the light quantum of third level and the light quantum of fourth level in a pipeline filled with a single fluid medium;
detecting a single-fluid-medium transmission quantity $N_{x,1}$ of the light quantum of first level, a single-fluid-medium transmission quantity $N_{x,2}$ of the light quantum of second level, a single-fluid-medium transmission quantity No of the light quantum of third level, and a single-fluid-medium transmission quantity $N_{x,4}$ of the light quantum of fourth level;
calculating a single-fluid-medium linear mass absorption coefficient $\alpha_{x,1}$ of the light quantum of first level from the medium-free transmission quantity $N_{0,1}$ and a single-fluid-medium photoelectric absorption equation of the light quantum of first level;
calculating a single-fluid-medium linear mass absorption coefficient $\alpha_{x,2}$ of the light quantum of second level from medium-free transmission quantity $N_{0,2}$ and a single-fluid-medium photoelectric absorption equation of the light quantum of second level;
calculating a single-fluid-medium linear mass absorption coefficient of the light quantum of third level $\alpha_{x,3}$ from the medium-free transmission quantity $N_{0,3}$ and a single-fluid-medium photoelectric absorption equation of the light quantum of third level; and
obtaining a Compton scattering constant K from a Compton scattering characteristic of the light quantum of fourth level.

5. The method for measuring a sand content in a miscible phase fluid according to claim 4, wherein the step of calculating a single-fluid-medium linear mass absorption coefficient $\alpha_{x,1}$ of the light quantum of first level from the medium-free transmission quantity $N_{0,1}$ and a single-fluid-medium photoelectric absorption equation of the light quantum of first level comprises:
transforming a photoelectric absorption total equation of the light quantum of first level for the at least two fluid media into a single-fluid-medium photoelectric absorption equation $$\ln\left(\frac{N_{0,1}}{N_{x,1}}\right) = \alpha_{x,1} Q_x;$$

and
introducing the medium-free transmission quantity $N_{0,1}$ and the single-fluid-medium transmission quantity $N_{x,1}$ into the photoelectric absorption total equation of the light quantum of first level for the at least two fluid media to obtain the single-fluid-medium linear mass absorption coefficient of the light quantum of first level $$\alpha_{x,1} = \ln\left(\frac{N_{0,1}}{N_{x,1}}\right)/Q_x.$$

6. The method for measuring a sand content in a miscible phase fluid according to claim 5, wherein the step of calculating linear masses of the at least two fluid media from the measured transmission quantity, the ratio between medium-free transmission quantities, the linear mass absorption coefficient and the Compton scattering constant comprises:
introducing the measured transmission quantity, the ratio between medium-free transmission quantities, the linear mass absorption coefficient and the Compton scattering constant into the photoelectric absorption total equation of the light quantum of first level for the at least two fluid media, a photoelectric absorption total equation of the light quantum of second level for the at least two fluid media, a photoelectric absorption total equation of the light quantum of third level for the at least two fluid media and a Compton absorption equation of the light quantum of fourth level, respectively, to calculate a linear mass of each of the at least two fluid media $Q_x$.

7. The method for measuring a sand content in a miscible phase fluid according to claim 6, further comprising, before the step of calculating a sand content in mass fraction in the miscible phase fluid based on the linear masses of the at least two fluid media:

judging whether the linear mass of a fluid medium of the at least two fluid media $Q_x$ comprise a linear sand mass $Q_s$ of a solid phase sand;

determining that the fluid medium in the miscible phase fluid comprises the solid phase sand when comprising the linear sand mass $Q_s$; and determining that the fluid medium in the miscible phase fluid comprises no solid phase sand when not comprising the linear sand mass $Q_s$.

8. The method for measuring a sand content in a miscible phase fluid according to claim 7, wherein the step of calculating a sand content in mass fraction in the miscible phase fluid based on the linear masses of the at least two fluid media further comprises:

calculating the sand content in mass fraction from the linear sand mass $Q_s$ of the solid phase sand and the linear mass $Q_x$ of all the at least two fluid media;

the sand content in mass fraction is $$SMF = \frac{Q_s}{Q_x}.$$

9. A device for measuring a sand content in a miscible phase fluid, comprising:

the phase separator installed on the pipeline, wherein the miscible phase fluid from the oil and gas well flows through the pipeline, and the phase separator is configured to carry out the method for measuring a sand content in a miscible phase fluid according to claim 1 to obtain the sand content in mass fraction in the miscible phase fluid.

* * * * *